United States Patent [19]

Watanabe et al.

[11] Patent Number: 5,786,387
[45] Date of Patent: Jul. 28, 1998

[54] LIPID DOUBLE-CHAIN DERIVATIVE CONTAINING POLYOXYETHYLENE

[75] Inventors: Hiroshi Watanabe; Kumi Taniguchi; Chikako Udagawa; Takashi Ando; Satoru Nakabayashi, all of Yokohama, Japan

[73] Assignee: Meiji Seika Kabushiki Kaisha, Tokyo-to, Japan

[21] Appl. No.: 553,601

[22] PCT Filed: Mar. 23, 1995

[86] PCT No.: PCT/JP95/00535

§ 371 Date: Jan. 25, 1996

§ 102(e) Date: Jan. 25, 1996

[87] PCT Pub. No.: WO95/25764

PCT Pub. Date: Sep. 28, 1995

[30] Foreign Application Priority Data

Mar. 23, 1994 [JP] Japan ................................. 6-052181
Dec. 6, 1994 [JP] Japan ................................. 6-302165

[51] Int. Cl.$^6$ .......................... A61K 31/225; A61K 31/23; C07C 59/235; C07C 233/05
[52] U.S. Cl. ..................... 514/547; 514/558; 514/563; 514/616; 424/450; 424/484; 436/71; 554/35; 554/36; 554/37; 554/61; 554/63; 554/64; 554/213; 554/219; 554/227; 564/153

[58] Field of Search ................... 554/36, 35, 61, 554/37, 63, 64, 213, 219, 227; 514/547, 558, 563, 616; 424/450, 484; 436/71; 564/153

[56] References Cited

U.S. PATENT DOCUMENTS 4,803,010  2/1989  Ogino et al. ............... 252/174.21

FOREIGN PATENT DOCUMENTS

| 64-14236 | 1/1989 | Japan . |
| 2-245025 | 9/1990 | Japan . |
| 3-287545 | 12/1991 | Japan . |
| 6-206830 | 7/1994 | Japan . |
| 6-206832 | 7/1994 | Japan . |

*Primary Examiner*—Shailendra Kumar
*Attorney, Agent, or Firm*—Wenderoth, Lind & Ponack

[57] ABSTRACT

A compound represented by the formula (I) is disclosed. The compound of the formula (I) is useful as a fine particle drug carrier. When used as the fine particle drug carrier, the compound efficiently avoids a reticuloendothelial system and has a long circulation time in blood.

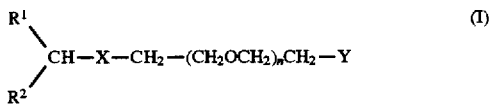

17 Claims, 1 Drawing Sheet

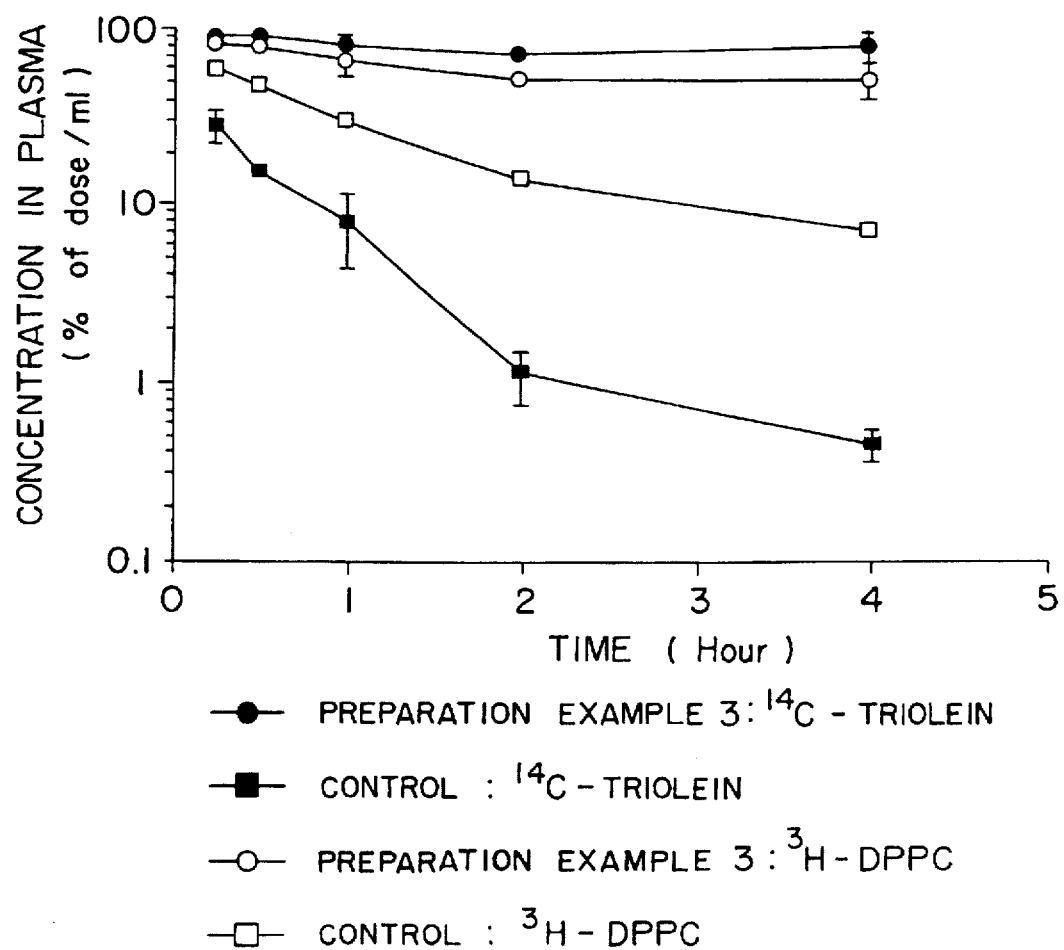
F I G. 1

LIPID DOUBLE-CHAIN DERIVATIVE CONTAINING POLYOXYETHYLENE

This application is a 371 of PCT/US95/00535, filed Mar. 23, 1995.

BACKGROUND OF THE INVENTION

1. Field of the Invention

The present invention relates to a lipid double-chain derivative containing a polyoxyethylene ("POE"). More specifically, it relates to a lipid double-chain derivative containing a polyoxyethylene which can be utilized as a fine particle drug carrier such as a mixed micell or a lipid emulsion or a liposome.

2. Description of the Related Art

In recent years, research and development have been conducted on a passive or an active target directional type drug delivery system in which an emulsified composition such as a liposome or a lipid emulsion containing a drug can be delivered. The research aims to selectively deliver a drug with a carrier to a target tissue, thereby heightening the concentration of the drug in the pathological tissue and reducing a side effect of the drug in the other tissues. Therefore, the efficacy of the drug can be enhanced. With regard to a fine particle carrier such as a lipid emulsion, the technical development of the following two points (a) and (b) is important.

(a) The development of a means for avoiding a reticuloendothelial system and improving circulation time in blood in order to enhance a drug delivery efficiency to a pathological tissue.

(b) The development of super fine particles which are stable in blood and capable of efficiently leaking a drug from a site, where vascular permeability is accelerated, to a pathological tissue outside blood vessels.

There has been, for example, proposed a liposome using a compound obtained by amide-bonding a carboxylic acid derivative of a polyoxyethylene to the amine moiety of phosphatidyl ethanolamine to improve its half-life period in blood and low circulating properties [Biochim. Biophys. Acta. 1066, p. 29 (1991)]. However, it is difficult to obtain stable and super-fine particles having an average particle diameter of 100 nm or less because of its high curvature. Further, the liposome has a drawback that the amount of the drug which can be delivered is limited.

With regard to the lipid emulsion, Japanese Patent Laid-open Publication No. 161430/1991 has disclosed that stable and super-fine particles having an average particle diameter of 50 nm or less can be obtained by the use of a water-soluble POE-containing lipid single-chain emulsion. However, it has been presumed that the effective circulation time in blood cannot always be obtained in blood by the single-chain surface active agent. Furthermore, Japanese Patent Laid-open Publication No. 203/1990 has disclosed that super-fine lipid emulsion particles can be obtained by adjusting the content ratio of a composite lipid such as lecithin which is a surface active component to a high level of 15 to 70%. However, this lipid emulsion does not always have a long circulation time in blood [Japanese Patent Laid-open Publication No. 203/1990, FIG. 2, and The Pharmaceutical Society of Japan, 108th Annual Meeting, P. 590 (1988)].

In addition, it is, in general, difficult to obtain the super-fine lipid emulsion particles which have a high curvature but which, on the other hand, have a high stability during storage and a high stability in blood only by the use of a lipid double-chain surface active substance (particularly a conical molecule-like surface active component).

As the fine particle carriers, in particular the liposomes, having the good circulation time in blood, there have been researched and developed a glycolipid [Boichim. Biophys. Acta. 981, p. 27 (1989), and U.S. Pat. No. 4,837,028 (Jun. 6, 1989)], a glycoprotein [Chem. Pharm. Bull., 36, p. 4187 (1988)], and the above POE derivatives of phosphatidyl ethanolamine [Biochim. Biophys. Acta. 1066, p. 29 (1991)]. However, it is considered that in all of these carriers, room for improvement still remains from the viewpoints of an industrial productivity and usefulness such as mass-productivity and cost.

SUMMARY OF THE INVENTION

We have now found that a certain kind of lipid derivative is useful as a fine particle drug carrier.

Accordingly, an object of the present invention is to provide a novel compound useful as a fine particle drug carrier.

Another object of the present invention is to provide a novel compound which efficiently avoids a reticuloendothelial system and which has a long circulation time in blood, when used as the fine particle drug carrier.

Still another object of the present invention is to provide a novel compound which realizes stable and super-fine particles having an average particle diameter of 100 nm or less, when used as the fine particle drug carrier.

Thus, according to the present invention, there provides a novel compound represented by the following formula (I):

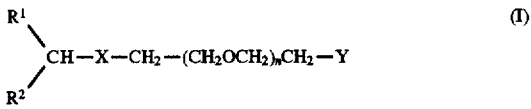

wherein $R^1$ represents a straight-chain alkyl group having 8 to 24 carbon atoms, a straight-chain alkenyl group having 8 to 24 carbon atoms, $R^3$—O—$(CH_2)$—, $R^3$—CO—O—$(CH_2)$—, $R^3$—O—CO—$(CH_2)_m$— or R3—CO—NH—$(CH_2)_m$— where $R^3$ represents a straight-chain alkyl group having 7 to 24 carbon atoms or a straight-chain alkenyl group having 7 to 24 carbon atoms, and m is an integer of 1 to 6;

$R^2$ represents a straight-chain alkyl group having 8 to 24 carbon atoms, a straight-chain alkenyl group having 8 to 24 carbon atoms, $R^3$—O—, $R^3$—CO—O— or $R^3$—O—CO— where $R^3$ is as defined above;

X represents —CO—NH—, —CO—O—, —NH—CO—$CH_2$—O— or —$CH_2$—O—CO—$CH_2$—O—, provided that, when X represents —CO—O—, $R^1$ and $R^2$ do not represent $R^3$—O—CO—$(CH_2)_m$— or $R^3$—O—CO—; when X represents —NH—CO—$CH_2$—O—, $R^1$ and $R^2$ independently represent $R^3$—O—CO—$(CH_2)_m$— or $R^3$—O—CO—; when X represents —$CH_2$—O—CO—$CH_2$—O—, $R^1$ represents a straight-chain alkyl group having 8 to 24 carbon atoms or a straight-chain alkenyl group having 8 to 24 carbon atoms and $R^2$ represents a straight-chain alkyl group having 8 to 24 carbon atoms or a straight-chain alkenyl group having 8 to 24 carbon atoms;

Y represents a hydroxyl group, a straight-chain or branched alkoxy group having 1 to 6 carbon atoms, or a carboxyl group which may be protected, and n is an integer of 10 to 230.

Furthermore, according to the present invention, there provides a fine particle drug carrier which comprises a compound represented by the formula (I).

BRIEF DESCRIPTION OF THE DRAWING

FIG. 1 shows a loss velocity- of an oil component ($^{14}$C-triolein) and a membrane component ($^3$H-DPPC) of a lipid emulsion according to the present invention in blood plasma.

DETAILED DESCRIPTION OF THE INVENTION

Compound

As a straight-chain $C_{8-24}$ alkyl group or alkenyl group represented by $R^1$ and $R^2$ in the formula (1), a straight-chain $C_{12-20}$ alkyl group or alkenyl group is preferable.

Further, $R^1$ may be $R^3$—O—$(CH_2)$—, $R^3$—CO—O—$(CH_2)$—, $R^3$—O—CO—$(CH_2)$m— or $R^3$—CO—NH—$(CH_2)$m—, wherein $R^3$ is a straight-chain $C_{7-24}$ alkyl group or alkenyl group, preferably a straight-chain $C_{8-20}$ alkyl group or alkenyl group, and m is an integer of 1 to 6, preferably 1 to 4.

Furthermore, $R^2$ may be $R^3$—O—, $R^3$—CO—O—, $R^3$—O—CO— or $R^3$—O—NH wherein $R^3$ is as defined above.

Further, X represents —CO—NH—, —CO—O—, —NH—CO—$CH_2$—O— or —$CH_2$—O—CO—$CH_2$—O—, preferably —CO—O— or —CO—NH—. However, when X represents —CO—O—, $R^1$ and $R^2$ do not represent $R^3$—O—CO—$(CH_2)_m$— or $R^3$—O—CO—. When X represents —NH—CO—$CH_2$—O—, $R^1$ and $R^2$ independently represent $R^3$—O—CO—$(CH_2)_m$— or $R^3$—O—CO—. When X represents —$CH_2$—O—CO—$CH_2$—O—, $R^1$ represents a straight-chain alkyl group having 8 to 24 carbon atoms or a straight-chain alkenyl group having 8 to 24 carbon atom and $R^2$ represents a straight-chain alkyl group having 8 to 24 carbon atoms or a straight-chain alkenyl group having 8 to 24 carbon atoms.

A $C_{1-6}$ alkoxy group represented by Y may be straight-chain or branched, preferably a $C_{1-4}$ alkoxy group. A carboxyl group represented by Y may be protected by a protective group. Examples of the protective group include a benzyl group and a t-butyl group.

In the formula (1), n is an integer of 10 to 230, preferably an integer of 15 to 200. The molecular weight of a polyoxyethylene moiety, i.e., a ($CH_2OCH_2$) moiety is 44, and therefore that n is in the range of 10 to 230 means that the molecular weight of the polyoxyethylene moiety is in the range of 440 to 10120.

Preparation of Compound

A compound represented by the formula (I) according to the present invention can be preferably prepared by any of the following methods.

Method (A)

A compound represented by the formula (I) in which X is —CO—O— can be prepared by treating a compound represented by the formula (II):

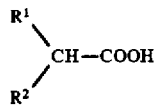
(II)

wherein $R^1$ and $R^2$ are as defined above, with thionyl chloride to form an acid chloride, and then reacting this acid chloride with a polyoxyethylene represented by the formula (III):

$HOCH_2$—$(CH_2OCH_2)$—$CH_2Y$      (III)

wherein Y and n are as defined above, in the presence or absence of a base (e.g., an inorganic base such as sodium bicarbonate or potassium carbonate, or an organic base such as triethylamine or pyridine) in an inert solvent (e.g., methylene chloride, tetrahydrofuran, toluene or N,N-dimethylformamide). If necessary, a protective group for a carboxyl group of the group Y can be removed in an ordinary manner.

Method (B)

A compound represented by the formula (I) in which X is —CO—O— can be prepared by carrying out dehydration reaction between a compound of the formula (II) and a compound of the formula (III) in the presence of a dehydrating/condensing agent (e.g., N,N'-dicyclohexylcarbodiimide or 1,1'-carbonyldiimidazole) in an inert solvent (e.g., methylene chloride, tetrahydrofuran, toluene or N,N-dimethylformamide). If necessary, a protective group for a carboxyl group of the group Y can be removed in an ordinary manner.

Method (C)

A compound represented by the formula (I) in which X is —CO—O— can also be prepared by reacting a compound of the formula (II) with an active ester of -a compound of the formula (III). The active ester can be obtained by reacting the compound of the formula (II) with, for example, N-hydroxysuccinimide. If necessary, a protective group for a carboxyl group of the group Y can be removed in an ordinary manner.

Method (D)

A compound represented by the formula (I) in which X is —CO—NH— can be prepared by obtaining an acid chloride of a compound of the formula (II) in the same manner as in the method (A) or an active ester of the compound of the formula (II) in the same manner as in the above-mentioned method (C), and then reacting the acid chloride or the active ester with a polyoxyethyleneamine derivative of the formula (IV):

$H_2N$—$CH_2$—$(CH_2OCH_2)_n$—$CH_2Y$      (IV)

wherein Y and n are as defined above, in an inert solvent (e.g., methylene chloride, tetrahydrofuran, toluene or N,N-dimethylformamide). If necessary, a protective group for a carboxyl group of the group Y can be removed in an ordinary manner.

Method (E)

A compound represented by the formula (I) in which X is —NH—CO— can be prepared by reacting a compound represented by the formula (V):

(V)

with a carboxymethylated polyoxyethylene derivative represented by the formula (VI):

$HOCOCH_2$—O—$CH_2$—$(CH_2OCH_2)_n$—$CH_2Y$      (VI)

wherein Y and n are as defined above, in accordance with any of the methods (A) to (C). If necessary, a protective group for a carboxyl group of the group Y can be removed in an ordinary manner.

Method (F)

A compound represented by the formula (I) in which X is —$CH_2$—O—CO—$CH_2$—O— can be prepared by reacting a compound represented by the formula (VII):

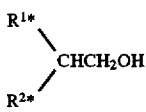

(VII)

wherein each of $R^{1*}$ and $R^{2*}$ is independently a straight-chain $C_{8-24}$ alkyl group or a straight-chain $C_{8-24}$ alkenyl group, with a compound of the formula (VI) in accordance with any of the methods (A) to (C).

A compound represented by the formula (II) in which each of $R^1$ and $R^2$ is independently the straight-chain $C_{8-24}$ alkyl group or the straight-chain $C_{8-24}$ alkenyl group can be prepared by reacting a compound represented by the formula (VIII):

$$R^{1*}-CH_2-COOH \quad (VIII)$$

wherein $R^{1*}$ is as defined above, with a straight-chain $C_{8-24}$ alkyl halide or a straight-chain $C_{8-24}$ alkenyl halide in the presence of a strong base in an inert solvent (e.g., N,N-dimethylformamide). The amount of the alkyl halide or the alkenyl halide is preferably in the range of 0.8 to 3 mols, more preferably 1.0 to 2.0 mols per mol of the compound of the formula (VIII).

The compound represented by the formula (II) in which each of $R^1$ and $R^2$ is the straight-chain $C_{8-24}$ alkyl group or the straight-chain $C_{8-24}$ alkenyl group can also be prepared by reacting a malonic diester represented by the formula (IX):

(IX)

wherein Z is an ester-forming group which is preferably a benzyl group or a t-butyl group, with a straight-chain $C_{8-24}$ alkyl halide or a straight-chain $C_{8-24}$ alkenyl halide in the presence of a strong base in an inert solvent (e.g., N,N-dimethylformamide). The amount of the alkyl halide or the alkenyl halide is preferably in the range of 1.5 to 4 mols, more preferably 2.0 to 3.0 mols per mol of the compound of the formula (IX).

The compound of the formula (II) can be converted into a compound represented by the formula (VII) by the use of a reducing agent having a carboxyl group such as diborane which has usually been used.

Furthermore, a compound represented by the formula (II) in which $R^1$ is a $R^3$—CO—O—CH$_2$— group and $R^2$ is a $R^3$—CO—O— group can be prepared by reacting a glyceraldehyde dialkyl acetal represented by the formula (X):

(X)

wherein $R^4$ is a lower alkyl group such as methyl or ethyl, with a fatty acid halide represented by the formula $R^3$CO—Hal wherein $R^3$ is as defined above, and Hal is a halogen, or a fatty acid active ester represented by the formula $R^3$COOR$^5$ wherein $R^3$ is as defined above, and $R^5$ is a leaving group (e.g., succinimide or p-nitrophenyl), in the presence of an organic base (e.g., triethylamine or pyridine) in an inert solvent (e.g., methylene chloride or acetonitrile), removing an acetal group therefrom in a usual manner, and then oxidizing the reaction product with a formed aldehyde oxidizing agent (e.g., permanganate). The amount of the fatty acid halide or the fatty acid active ester is preferably in the range of 1.5 to 4 mols, more preferably 2.0 to 3.0 mols per mol of the compound of the formula (X).

A compound represented by the formula (II) in which $R^1$ is a $R^3$—O—CH$_2$— group and $R^2$ is a $R^3$—O— group can be prepared by converting a glyceraldehyde dialkyl acetal of the formula (X) into a 2,3-di-O-alkyl (or alkenyl) glyceraldehyde dialkyl acetal in accordance with a method described in Japanese Patent Laid-Open Publication No. 504286/1991, removing an acetal group therefrom in a usual manner, and then oxidizing the reaction product with a formed aldehyde oxidizing agent (e.g., permanganate).

A compound represented by the formula (II) in which $R^1$ is a $R^3$—CO—NH—(CH$_2$)$_m$— group and $R^2$ is a $R^3$—CO—NH— group can be obtained by reacting an amino acid represented by the formula (XI):

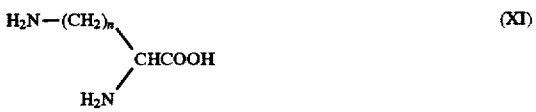

(XI)

with a compound represented by the formula $R^3$COOH (wherein $R^3$ is as defined above) in the presence of a base (e.g., an inorganic base such as sodium hydroxide, or an organic base such as triethylamine or N-methylmorpholine) in a solvent (e.g., water or ethanol) in accordance with a mixed acid anhydride method, an active ester method or a dehydration condensation method which has been conventionally used.

A compound represented by the formula (V) in which $R^1$ is a $R^3$—O—CO—(CH$_2$)$_m$— group and $R^2$ is a $R^3$—O—CO— group can be obtained by reacting a compound represented by the formula (XII):

(XII)

wherein P is a protective group for an amino group such as benzyloxycarbonyl or t-butoxycarbonyl, with a compound represented by the formula $R^3$COOH (wherein $R^3$ is as defined above) in the presence of an organic base (e.g., triethylamine or N-methylmorpholine) in an inert solvent (e.g., methylene chloride, acetonitrile or N,N-dimethylformamide) in accordance with a mixed acid anhydride method, an active ester method or a dehydration condensation method which has been conventionally used, and then removing the protection of the amino group.

The polyoxyethylene derivatives represented by the formulae (III), (IV) and (VI) can be synthesized according to the description in Eur. Polym. J., 19, p. 1177 (1983) and Tetrahedron, 40, p. 1581 (1984).

Drug carrier

The compound of the formula (I) according to the present invention can be used for the preparation of a fine particle drug carrier. In particular, this compound can be used for the preparation of the fine particle drug carrier in the form of lipid emulsion, liposome or micell. Therefore, according to the present invention, the fine particle drug carrier utilizing the compound of the formula (I) can be provided.

The fine particle drug carrier according to the present invention resists its uptake by reticuloendothelial system, so that the carrier has excellent circulation time in blood and is stable in the blood.

Furthermore, in the fine particle drug carrier of the present invention, its average particle diameter can be suitably altered by changing a composition ratio of the compound of the formula (I) to another component. In particular, the fine particle drug carrier having an average particle diameter of 100 nm or less, preferably 50 nm or less can be prepared by the use of the compound of the formula (I) according to the present invention. The super-fine particles having an average particle diameter of 100 nm or less, preferably 50 nm or less is advantageous, because they can selectively leak from inflammatory sites, particularly sites of neoplastic blood vessels of which permeability is accelerated and, thus, they can easily transfer to a pathological tissue.

According to a preferred embodiment of the present invention, the fine particle drug carrier of the present invention can be in the form of a lipid emulsion. This lipid emulsion basically comprises the compound of the formula (I), a lipid such as soybean oil which becomes a core, and a fat-soluble drug which is carried by this lipid. The lipid emulsion can be prepared in accordance with any of known preparation methods of lipid emulsions. The lipid emulsion of the present invention may further contain glycerin, sugar or sugaralcohol for the establishment of an isotonic state or stabilization; a phospholipid; and a surface active agent for controlling various characteristics.

The particle diameter of the super-fine particles in the lipid emulsion can be controlled by changing a weight ratio of the total surface active agents to the lipid including a fat-soluble drug. In general, when the weight ratio of the total surface active agents to the lipid is 1.5 or less, preferably 0.2 to 1.2, an average particle diameter of 100 nm can be realized. When another surface active agent is used together with the compound of the formula (I), a molar ratio of the compound of the formula (I) to the total surface active agents is preferably 1/20 or more.

The fine particle drug carrier of the present invention can be in the form of a liposome. This liposome can be prepared by mixing the compound of the formula (I), a phospholipid (e.g., phosphatidyl choline, sphingomyelin or phosphatidyl ethanolamine), and then carrying out a known procedure (e.g., Ann. Rev. Biophys. Bioeng., Vol. 9, p. 467 (1980)). The liposome of the present invention may contain cholesterol; a dialkyl phosphate such as sodium dicetylphosphate; a positive charge interface substance such as stearylamine; and an antioxidant such as tocopherol to control various characteristics.

Furthermore, the fine particle drug carrier of the present invention can be in the form of a micell. This micell can be prepared by mixing the compound of the formula (I) with a surface active agent (e.g., a polyoxysorbitan fatty acid ester or a salt of a fatty acid), and then carrying out a known procedure to form a micell.

There is no limitation on a drug which is carried by the fine particle drug carrier of the present invention, but it is preferred to select the suitable fine particle drug carrier in compliance with the characteristics of the drug. Specifically, the characteristics of the drug to which the liposome can be applied are not limited, but the lipid emulsion and the micell can be applied to fat-soluble drugs and fat-soluble derivatives.

Typical examples of the drug which can be carried by the fine particle drug carrier of the present invention include anticancer drugs, anti-inflammatory drugs, antibacterial drugs, antifungal drugs, painkillers, hypotensives, vasodilators, bronchodilators, anti-ulcer drugs, vitamin drugs, hormone drugs, anti-allergy drugs, immunologic inhibitors and diagnosis drugs. The fine particle drug carrier of the present invention is particularly effective for a disease locally present in a specific tissue site. Therefore, the fine particle drug carrier of the present invention can effectively be applied to a therapeutic drug or a diagnosis drug regarding an inflammatory disease, a cancer, a vascular disease or an immunologic disease. Examples of the preferably applicable drugs include anticancer drugs such as adriamycin, methotrexate and their water-soluble and fat-soluble prodrug derivatives; antibacterial drugs such as penicillin and cephalosporin; immunologically active drugs such as steroid and prostaglandin; and other physiologically active substances such as insulin and interferon.

EXAMPLES

The present invention will be described in more detail with reference to examples, but the present invention should not be limited to these examples.

Reference Example 2-cetyl-octadecanoic acid

Sodium hydride (60%, NaH, 4.2 g) was added to an N,N-dimethylformamide (50 ml) containing 10 g of dibenzyl malonate, and the mixture was then stirred for 10 minutes. After 23.6 ml of 1-bromohexadecane (cetyl bromide) was added thereto, the solution was then stirred at room temperature for 1 hour. Next, water and ethyl acetate were added, followed by extraction. After the resultant organic layer was dried, the solvent was distilled off under reduced pressure. The residue was purified by silica gel column chromatography (n-hexane:ethyl acetate=100:1) to obtain 7.3 g of a dicetyl substance. After 3.18 g of this dicetyl substance was mixed with 90 ml of ethanol and 3 ml of toluene, 300 mg of 10% palladium-carbon was added to the solution to carry out catalytic reduction (a hydrogen gas, 1 atm) at room temperature for 4 hours, thereby removing a benzyl group. After the removal of the catalyst by filtration, the solvent was distilled off under reduced pressure to obtain dicarboxylic acid. Furthermore, the dicarboxylic acid thus obtained is heated at 150° C. for 7 hours in the absence of any solvent for decarboxylation to remove carbodioxide, thereby obtaining 2.3 g of a monocarboxylic acid (compound 1).

$R_F$=0.77 (CHCl$_3$:MeOH=20:1)

$^1$H-NMR (CDCl$_3$) δ: 0.88 (t, 6H), 1.2–1.35 (m, 56H), 1.42–1.51 (m, 2H), 1.57–1.65 (m, 2H), 2.31–2.38 (m, 1H).

Example 1 ω-methyl-polyoxyethylene 2-cetyl-octadecanoate

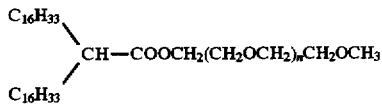

A tetrahydrofuran (THF, 1 ml) solution containing 100 mg (0.2 mmol) of a monocarboxylic acid compound (the compound obtained in Reference Example) and 39 mg (0.24 mmol) of 1,1'-carbonyldiimidazole was stirred at 70° C. for 1 hour. To this reaction solution were added 1 ml of a tetrahydrofuran solution containing 132 mg (0.24 mmol) of α-hydro-ω-methoxypoly(oxyethylene) (average molecular weight=550) and a catalystic amount of sodium ethoxide, and the solution was further stirred at 70° C. overnight. After the solvent was distilled off under reduced pressure, the residue was purified by silica gel column chromatography (chloroform:methanol=50:1) to obtain 124 mg of the title compound in which the average molecular weight of a ω-methyl-polyoxyethylene moiety was 550.

$R_F$=0.53 (CHCl$_3$:MeOH=20:1)

$^1$H-NMR (CDCl$_3$) δ: 0.88 (t, 6H), 1.2–1.35 (m, 56H), 1.33–1.47 (m, 2H), 1.53–1.65 (m, 2H), 2.31–2.38 (m, 1H), 3.38 (s, 3H), 3.65 (m), 4.23 (t, 2H).

9

Example 2 ω-methyl-polyoxyethylene 2-cetyl-octadecanoate

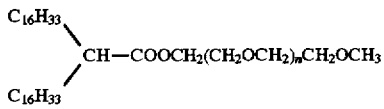

A tetrahydrofuran (THF, 20 ml) solution containing 2.00 g (3.93 mmol) of a monocarboxylic acid compound (the compound obtained in Reference Example) and 1.27 g (7.86 mmol) of 1,1'-carbonyldiimidazole was stirred at 70° C. for 3 hours. To this reaction solution were added 20 ml of a tetrahydrofuran solution containing 7.47 g (3.93 mmol) of α-hydro-ω-methoxypoly(oxyethylene) (average molecular weight=1900) and a catalystic amount of potassium t-butoxide, and the solution was further stirred at 70° C. for 3 hours. After the solvent was distilled off under reduced pressure, the residue was purified by silica gel column chromatography (chloroform:methanol=15:1) to obtain 7.03 g of the title compound in which the average molecular weight of a ω-methyl-polyoxyethylene moiety was 1900.

$R_f$=0.33 (CHCl$_3$:MeOH=10:1)

$^1$H-NMR (CDCl$_3$) δ: 0.88 (t, 6H), 1.2–1.35 (m, 56H), 1.33–1.47 (m, 2H), 1.53–1.65 (m, 2H), 2.31–2.38 (m, 1H), 3.38 (s, 3H), 3.64 (m), 4.23 (m, 2H).

Example 3 N-ω-methyl-polyoxyethylene 2-cetyl-octadecanoic amide

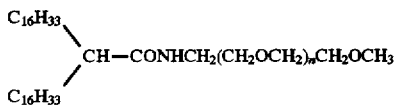

In 15 ml of thionyl chloride was dissolved 1.27 g of a monocarboxylic acid compound (the compound obtained in Reference Example), and the solution was then stirred at 50° C. for 4 hours and further at room temperature overnight. After volatile components such as thionyl chloride were distilled off, 50 ml of 1,2-dichloroethane, 4.75 g of α-methyl-ω-aminopoly(oxyethylene) (average molecular weight=1900) and 0.42 ml of triethylamine were then added to the solution. After stirring at room temperature for 3 days, the solution was concentrated. The residue was purified by silica gel column chromatography (chloroform:methanol= 30:1), and additional purification was done by gel column chromatography (methanol=100%) using LH-20 to obtain 2.5 g of the title compound in which the average molecular weight of a ω-methyl-polyoxyethylene moiety was 1900.

$R_f$=0.77 (CHCl$_3$:MeOH=20:1)

$^1$H-NMR (CDCl$_3$) δ: 0.88 (t, 6H), 1.2–1.32 (m, 56H), 1.33–1.43 (m, 2H), 1.53–1.63 (m, 2H), 1.94–2.02 (m, 1H), 3.38 (s, 3H), 3.64 (m), 6.07 (bt, 1H).

Example 4 ω-methyl-polyoxyethylene α,α-dioleylacetate

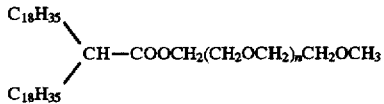

Sodium hydride (60%, NaH, 0.67 g) was added to an N,N-dimethylformamide (30 ml) solution containing 2.6 g of di-t-butyl malonate, and the solution was then stirred for 10 minutes. A 11 g of 1-iodo-cis-9-octadecene was added, followed by stirring at room temperature for 8 hours.

10

Furthermore, 0.33 g of sodium hydride was added, and the solution was stirred at room temperature overnight to carry out reaction. Afterward, water and ethyl acetate were added, followed by extraction. The resultant organic layer was dried, and the solvent was then distilled off under reduced pressure. The residue was purified by silica gel column chromatography (n-hexane:ethyl acetate=70:1) to obtain 5.7 g of an α,α-dioleyl substance [$R_f$=0.66 (n-hexane:ethyl acetate=20:1)].

A 3 g of this di-t-butyl dioleylmalonate was dissolved in a solution comprising 20 ml of anisole, 20 ml of dichloromethane and 10 ml of trifluoroacetic acid, followed by stirring at room temperature overnight. After reaction, volatile components were distilled off. The residue was then heated at 150° C. for 4 hours to remove carbonic acid, thereby obtaining 2.32 g of α,α-dioleylacetic acid [$R_f$=0.12 (chloroform:methanol=10:1)].

In 10 ml of thionyl chloride was dissolved 1.15 g of α,α-dioleylacetic acid, and after stirring at 80° C. for 6 hours, volatile components were distilled off. To the residue were added 15 ml of 1,2-dichloroethane, 3.34 g of dehydrated and dried α-hydro-ω-methoxypoly(oxyethylene) (average molecular weight=1900) and 244 μl of triethylamine, followed by stirring at room temperature overnight. After the reaction solution was concentrated, the residue was purified by silica gel column chromatography (chloroform:methanol=30:1; 20:1), thereby obtaining 700 mg of the title compound in which the average molecular weight of a ω-methyl-polyoxyethylene moiety was 1900.

$R_f$=0.77 (CHCl$_3$:MeOH=20:1)

$^1$H-NMR (CDCl$_3$) δ: 0.88 (t, 6H), 1.26 (m), 1.79–2.08 (m), 2.34 (m, 1H), 3.38 (s, 3H), 3.65 (m), 4.23 (m, 2H), 5.3–5.4 (m, 4H).

Example 5 N-ω-methyl-polyoxyethylene 2,3-di-O-palmitoyl-DL-glyceric amide

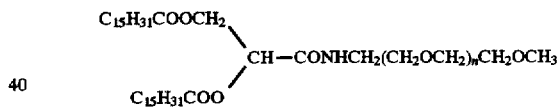

In 60 ml of 1,2-dichloroethane was dissolved 1.64 g of DL-glyceraldehyde diethyl acetal, and 6.6 g of palmitic acid chloride and 3.33 ml of triethylamine were further added thereto, followed by stirring at room temperature overnight. After hexane was added, insolubles were removed by filtration. The resultant filtrate was then concentrated, and the residue was purified by silica gel column chromatography (hexane:ethyl acetate=30:1) to obtain 3.5 g of a diester substance ($R_f$=0.25 (hexane:ethyl acetate=20:1).

A 3 g of this diester substance was dissolved in 150 ml of acetone, and 1.5 g of p-toluenesulfonic acid monohydrate was added, followed by stirring at 57° C. for 4 hours. The solution was extracted with an aqueous sodium hydrogencarbonate solution and ethyl acetate. The resultant organic layer was washed with water twice to obtain an ethyl acetate solution. The ethyl acetate solution thus obtained was dried over anhydrous sodium sulfate, and volatile components were then distilled off, thereby obtaining 2.7 g of an aldehyde substance [$R_f$=0.17 (toluene)].

In 50 ml of chloroform was dissolved 2.6 g of this aldehyde substance, and 3.37 g of tetra(n-butyl)ammonium permanganate was added, followed by stirring at room temperature for 1.5 hours. After hexane was added, insolubles were then removed by filtration, followed by water washing. The washed solution was purified by silica gel column chromatography (CHCl$_3$:MeOH=100:1) to obtain 772 mg of a carboxylic acid substance [R$_F$=0.16 (CHCl$_3$:MeOH=100:1)].

The same procedure as in Example 3 was carried out to obtain the title compound from the carboxylic acid substance R$_F$32 0.68 (CHCl$_3$:MeOH=5:1)

$^1$H-NMR (CDCl$_3$) δ: 0.88 (t, 6H), 1.25 (m), 1.57–1.69 (m, 4H), 2.29 (t), 2.40 (t), 2.41 (t), 3.38 (s, 3H), 3.64 (m), 4.37 (dd, 1H), 4.55 (dd, 1H), 5.41 (dd, 1H), 6.71 (m, 1H).

Example 6 Nα,Nε-dipalmitoyl-DL-lysine-N-ω-methylpolyoxyethyleneamide

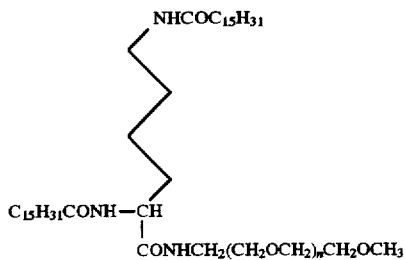

To 730 mg of DL-lysine was added 5 ml of a methanol solution of 1M n-tetrabutylammonium hydroxide, and after dissolution, methanol was distilled off under reduced pressure. A 20 ml of N,N-dimethylformamide, 4.2 ml of triethylamine and 5.3 g of N-palmitoyloxysuccinimide were further added, followed by stirring at room temperature for 4 days. After ethyl acetate was added to the reaction solution, the solution was filtrated. The resultant filtrate was washed with an acidic liquid, and then allowed to stand. The precipitate was collected by filtration to obtain 1.1 g of Nα,Nε-dipalmitoyl-DL-lysine [R$_F$=0.53 (CHCl$_3$:CH$_3$OH:H$_2$O=30:8:1)].

To 31.1 mg of this Nα,Nε-dipalmitoyl-DL-lysine were added 2 ml of tetrahydrofuran, 11.5 mg of N-hydroxysuccinimide and 20.6 mg of N,N'-dicyclohexylcarbodiimide, followed by stirring at 50° C. Furthermore, 95 mg of α-methyl-ω-aminopoly(oxyethylene) (average molecular weight=1900) was added to the solution, and stirring was made at room temperature overnight. After the solvent was distilled off under reduced pressure, the residue was purified by silica gel column chromatography (chloroform:methanol=20:1), thereby obtaining the above desired compound.

R$_F$=0.61 (CHCl$_3$:MeOH=5:1)

$^1$H-NMR (CDCl$_3$) δ: 0.88 (t, 6H), 1.25 (m), 1.53 (m, 2H), 1.61 (m, 6H), 1.80 (m, 2H), 2.16 (t, 2H), 2.22 (t, 2H), 3.23 (m, 2H), 3.38 (s, 3H), 3.65 (m), 4.40 (m, 1H), 5.95 (bt, 1H), 6.56 (bd, 1H), 6.96 (bt, 1H).

Preparation examples using compounds of the present invention will be described.

In the following preparation examples, an ultrasonic treatment was carried out by the use of a probe type ultrasonic homogenizer Branson Sonifive 250. A particle diameter of particles in a solution was measured by the use of a light-scattering particle diameter measuring device Nicomp 370.

Preparation Example 1

In 5 ml of a mixed solution of methylene chloride and methanol (volume ratio=2:1) were dissolved 50 mg of soybean oil, 25 mg of a compound obtained in Example 2 and 25 mg of L-α-dipalmitoylphosphatidyl choline. After the organic solvent was distilled off, 4.9 ml of a 0.24M aqueous glycerin solution was added to the resultant residue. The obtained solution was subjected to an ultrasonic treatment at 45° C. for 15 minutes. 100% of the obtained white transparent solution passed through a filtration membrane having a pore diameter of 0.22 μm. The particle diameter of particles in this solution showed a Gauss distribution, and its average particle diameter was 36 nm (data point=1000.4K).

Preparation Example 2

In 5 ml of a mixed solution of methylene chloride and methanol (volume ratio=2:1) were dissolved 50 mg of soybean oil, 25 mg of a compound obtained in Example 2 and 25 mg of yolk lecithin. After the organic solvent was distilled off, 4.9 ml of a 0.24M aqueous glycerin solution was added to the resultant residue. The obtained solution was subjected to an ultrasonic treatment at 45° C. for 15 minutes. 100% of the obtained white transparent solution passed through a filtration membrane having a pore diameter of 0.22 μm. The particle diameter of particles in this solution showed a Gauss distribution, and its average particle diameter was 35.9 nm (data point=1014.1K).

Preparation Example 3

In 5 ml of a mixed solution of methylene chloride and methanol (volume ratio=2:1) were dissolved 100 mg of triolein, 50 mg of a compound obtained in Example 3 and 50 mg of L-α-dipalmitoylphosphatidyl choline. After the organic solvent was distilled off, 9.8 ml of a 0.24M aqueous glycerin solution was added to the resultant residue. The obtained solution was subjected to an ultrasonic treatment at 35° C. for 60 minutes, and then allowed to stand at 35° C. for 60 minutes. 100% of the obtained white transparent solution passed through a filtration membrane having a pore diameter of 0.22 μm. The particle diameter of particles in this solution showed a Gauss distribution, and its average particle diameter was 28.3 nm (data point=1044.2K).

Preparation Example 4

In 5 ml of a mixed solution of methylene chloride and methanol (volume ratio=2:1) were dissolved 45 mg of triolein, 5 mg of tocopheryl acetate, 25 mg of a compound obtained in Example 2 and 25 mg of L-α-dipalmitoylphosphatidyl choline. After the organic solvent was distilled off, 4.9 ml of a 0.24M aqueous glycerin solution was added to the resultant residue. The obtained solution was subjected to an ultrasonic treatment at 55° C. for 7 minutes. 100% of the obtained white transparent solution passed through a filtration membrane having a pore diameter of 0.22 μm. The particle diameter of particles in this solution showed a Gauss distribution, and its average particle diameter was 36.1 nm (data point=1014.8K).

Preparation Example 5

In 5 ml of a mixed solution of methylene chloride and methanol (volume ratio=2:1) were dissolved 45 mg of triolein, 5 mg of dexamethasone palmitate, 25 mg of a compound obtained in Example 2 and 25 mg of L-α-dipalmitoylphosphatidyl choline. After the organic solvent was distilled off, 4.9 ml of a 0.24M aqueous glycerin solution was added to the resultant residue. The obtained solution was subjected to an ultrasonic treatment at 55° C. for 7 minutes. 100% of the obtained white transparent solution passed through a filtration membrane having a pore diameter of 0.22 μm. The particle diameter of particles in this solution showed a Gauss distribution, and its average particle diameter was 32.3 nm (data point=1018.3K).

Preparation Example 6

In 5 ml of a mixed solution of methylene chloride and methanol (volume ratio=2:1) were dissolved 50 mg of triolein, 25 mg of a compound obtained in Example 1 and 25 mg of L-α-dipalmitoylphosphatidyl choline. After the organic solvent was distilled off, 4.9 ml of a 0.24M aqueous glycerin solution was added to the resultant residue. The obtained solution was subjected to an ultrasonic treatment at 65° C. for 15 minutes. 100% of the obtained white transparent solution passed through a filtration membrane having a pore diameter of 0.22 μm. The particle diameter of particles in this solution showed a Gauss distribution, and its average particle diameter was 95.4 nm (data point= 1274.7K).

Preparation Example 7

In 5 ml of a mixed solution of methylene chloride and methanol (volume ratio=2:1) were dissolved 100 mg of triolein, 50 mg of a compound obtained in Example 2 and 50 mg of L-α-dipalmitoylphosphatidyl choline. After the organic solvent was distilled off, 9.8 ml of a 0.24M aqueous glycerin solution was added to the resultant residue. The obtained solution was subjected to an ultrasonic treatment at 35° C. for 30 minutes. 100% of the obtained white transparent solution passed through a filtration membrane having a pore diameter of 0.22 μm. The particle diameter of particles in this solution showed a Gauss distribution, and its average particle diameter was 34.2 nm (data point= 1120.1K).

Preparation Example 8

In 5 ml of a mixed solution of methylene chloride and methanol (volume ratio=2:1) were dissolved 100 mg of triolein, 25 mg of a compound obtained in Example 2 and 25 mg of L-α-dipalmitoylphosphatidyl choline. After the organic solvent was distilled off, 9.85 ml of a 0.24M aqueous glycerin solution was added to the resultant residue. The obtained solution was subjected to an ultrasonic treatment at 35° C. for 30 minutes. 100% of the obtained white transparent solution passed through a filtration membrane having a pore diameter of 0.22 μm. The particle diameter of particles in this solution showed a Gauss distribution, and its average particle diameter was 65.1 nm (data point=1016.6K)

Preparation Example 9

In 5 ml of a mixed solution of methylene chloride and methanol (volume ratio=2:1) were dissolved 90 mg of triolein, 15 mg of a compound obtained in Example 2 and 15 mg of L-α-dipalmitoylphosphatidyl choline. After the organic solvent was distilled off, 9.8 ml of a 0.24M aqueous glycerin solution was added to the resultant residue. The obtained solution was subjected to an ultrasonic treatment at 35° C. for 15 minutes. 100% of the obtained white transparent solution passed through a filtration membrane having a pore diameter of 0.22 μm. The particle diameter of particles in this solution showed a Gauss distribution, and its average particle diameter was 82.6 nm (data point= 1020.0K).

Preparation Example 10

In 5 ml of a mixed solution of methylene chloride and methanol (volume ratio=2:1) were dissolved 100 mg of triolein, 12.5 mg of a compound obtained in Example 2 and 12.5 mg of L-α-dipalmitoylphosphatidyl choline. After the organic solvent was distilled off, 9.88 ml of a 0.24M aqueous glycerin solution was added to the resultant residue. The obtained solution was subjected to an ultrasonic treatment at 35° C. for 15 minutes. 100% of the obtained white transparent solution passed through a filtration membrane having a pore diameter of 0.22 μm. The particle diameter of particles in this solution showed a Gauss distribution, and its average particle diameter was 94.2 nm (data point= 1474.7K).

Preparation Example 11

In 5 ml of a mixed solution of methylene chloride and methanol (volume ratio=2:1) were dissolved 100 mg of triolein, 10 mg of a compound obtained in Example 2 and 10 mg of L-α-dipalmitoylphosphatidyl choline. After the organic solvent was distilled off, 9.9 ml of a 0.24M aqueous glycerin solution was added to the resultant residue. The obtained solution was subjected to an ultrasonic treatment at 35° C. for 15 minutes. 100% of the obtained white transparent solution passed through a filtration membrane having a pore diameter of 0.22 μm. The particle diameter of particles in this solution showed a Gauss distribution, and its average particle diameter was 126.4 nm (data point= 1298.5K).

Preparation Example 12

In a mixed solution of dichloromethane and methanol (volume ratio=4:1) were dissolved 10 mg of a compound obtained in Example 2, 50 mg of L-α-dipalmitoylphosphatidyl choline and 50 mg of cholesterol. The organic solvent was gradually distilled off under reduced pressure by a rotary evaporator to form a lipid film on a glass wall of an eggplant type flask. Into this flask, 9.9 ml of a phosphoric acid-buffered physiological saline (pH= 7.4) was added. The solution was shaken and then subjected to an ultrasonic treatment at 45° C. for 60 minutes. After the solution was cooled to the room temperature, the solution was passed through a polycarbonate membrane filter having a pore diameter of 0.1 μm to give a transparent liposome solution containing particles of which average particle diameter was in the range of 70 to 80 nm. This liposome was stable at 60° C. for 1 month or more.

Comparative Example 1

In 5 ml of a mixed solution of methylene chloride and methanol (volume ratio=2:1) were dissolved 100 mg of triolein, 50 mg of polyoxyethylene monooleyl ether (average molecular weight=50) and 50 mg of L-α-dipalmitoylphosphatidyl choline. After the organic solvent was distilled off, 9.8 ml of a 0.24M aqueous glycerin solution was added to the resultant residue. The obtained solution was subjected to an ultrasonic treatment at 55° C. for 30 minutes. 100% of the obtained white transparent solution passed through a filtration membrane having a pore diameter of 0.22 μm. The particle diameter of particles in this solution showed a Gauss distribution, and its average particle diameter was 32 nm.

Table 1 shows a relation between a ratio of the amount of the total lipid (O) to that of the total surface active substance (S) and a particle diameter in each preparation example.

TABLE 1

| Average Particle Diameter of Lipid Emulsion | | |
| --- | --- | --- |
| Preparation Example | Ratio of O/S | Average Particle Diameter (nm) |
| 7 | 1 | 34.2 |
| 8 | 2 | 65.1 |
| 9 | 3 | 82.6 |
| 10 | 4 | 94.2 |
| 11 | 5 | 126.4 |

Biological Test

The particle of Preparation Example 3 and a control containing $^{14}C$-triolein (10 μCi) and $^{3}H$-dipalmitoylphosphatidyl choline (DPPC) (10 μCi) were used. These analytes were administered to mice (Balb/c, female, 7 weeks old) through their tail veins. These mice were then killed by bleeding after 15 minutes, 30 minutes, 1 hour, 2 hours and 4 hours. At each point of the respective times, blood plasma was sampled in a vial, and measurement was then made by the use of a liquid scintillation counter. The results of the measurement are shown in FIG. 1. With respect to the particle of the control, the concentration of $^{14}$C-triolein as a lipid component in the blood plasma rapidly decreased after 15 minutes from the administration. On the contrary, the concentration decrease of $^3$H-DPPC as a film component was slow, which was largely different from the behavior of the lipid component. In the control, circulation time in blood of the lipid component for delivering an oil-soluble drug were short. On the contrary, in the lipid emulsion of Preparation Example 3, the lipid component ($^{14}$C-triolein) and the film component ($^3$H-DPPC) behaved similarly, and therefore it was apparent that the particle of Preparation Example 3 was very excellent in circulation time in blood.

What is claimed is:

1. A compound represented by the following general formula (I)

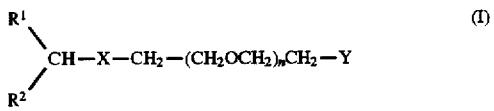

wherein $R^1$ represents straight-chain alkyl having 8 to 24 carbon atoms, straight-chain alkenyl having 8 to 24 carbon atoms, $R^3$—O—$(CH_2)$—, $R^3$—CO—O—$(CH_2)$—, $R^3$—O—CO—$(CH_2)_m$— or $R^3$—CO—NH—$(CH_2)_m$— where $R^3$ represents straight-chain alkyl having 7 to 24 carbon atoms or straight-chain alkenyl having 7 to 24 carbon atoms, and m is an integer of 1 to 6;

$R^2$ represents straight-chain alkyl having 8 to 24 carbon atoms, straight-chain alkenyl having 8 to 24 carbon atoms, $R^3$—O—, $R^3$—CO—O— or $R^3$—O—CO— where $R^3$ is as defined above;

X represents —CO—NH—, —CO—O—, —NH—CO—CH$_2$—O— or —CH$_2$—O—CO—CH$_2$—O—, provided that when X represents —CO—O—, $R^1$ and $R^2$ do not represent $R^3$—O—CO—$(CH_2)_m$— or $R^3$—O—CO—; when X represents —NH—CO—CH$_2$—O—, $R^1$ and $R^2$ independently represent $R^3$—O—CO—$(CH_2)_m$— or $R^3$—O—CO—; when X represents —CH$_2$—O—CO—CH$_2$—O—, $R^1$ represents straight-chain alkyl having 8 to 24 carbon atoms or straight-chain alkenyl having 8 to 24 carbon atoms and $R^2$ represents straight-chain alkyl having 8 to 24 carbon atoms or straight-chain alkenyl having 8 to 24 carbon atoms;

Y represents hydroxyl, straight-chain or branched alkoxy having 1 to 6 carbon atoms, or carboxyl which may be protected, and n is an integer of 10 to 230.

2. The compound according to claim 1 wherein $R^1$ is $C_{12-20}$ alkyl, $C_{12-20}$ alkenyl, $R^3$—C—O—$(CH_2)_m$— or $R^3$—CO—NH—$(CH_2)_m$—, $R^2$ is $C_{12-20}$ alkyl, $C_{12-20}$ alkenyl, $R^3$—CO—O— or $R^3$—CO—NH—, X is —CO—C— or —CO—NH—, and Y is hydroxyl or $C_{1-6}$ alkoxy.

3. The compound according to Claim 1 which is N-ω-methyl-polyoxyethylene 2-cetyl-octadecanoic amide in which the molecular weight of a polyoxyethylene moiety is about 1900.

4. The compound according to claim 1 which is ω-methyl-polyoxyethylene 2-cetyl-octadecanoate in which the molecular weight of a polyoxyethylene moiety is about 1900.

5. An emulsified composition comprising fine particles comprising the compound represented by the following formula (I)

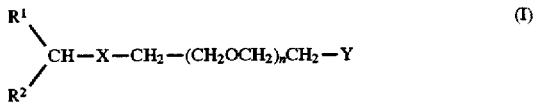

wherein $R^1$ represents straight-chain alkyl having 8 to 24 carbon atoms, straight-chain alkenyl having 8 to 24 carbon atoms, $R^3$—O—$(CH_2)$—, $R^3$—CO—O—$(CH_2)$—, $R^3$—O—CO—$(CH_2)_m$— or $R^3$—CO—NH—$(CH_2)_m$— where $R^3$ represents straight-chain alkyl having 7 to 24 carbon atoms or straight-chain alkenyl having 7 to 24 carbon atoms, and m is an integer of 1 to 6;

$R^2$ represents straight-chain alkyl having 8 to 24 carbon atoms, straight-chain alkenyl having 8 to 24 carbon atoms, $R^3$—O—, $R^3$—CO—O— or $R^3$—O—CO— where $R^3$ is as defined above;

X represents —CO—NH—, —CO—O—, —NH—CO—CH$_2$—O— or —CH$_2$—O—CO—CH$_2$—O—, provided that when X represents —CO—O—, $R^1$ and $R^2$ do not represent $R^3$—O—CO—$(CH_2)_m$— or $R^3$—O—CO—; when X represents —NH—CO—CH$_2$—O—, $R^1$ and $R^2$ independently represent $R^3$—O—CO—$(CH_2)_m$— or $R^3$—O—CO—; when X represents —CH$_2$—O—CO—CH$_2$—O—, $R^1$ represents straight-chain alkyl having 8 to 24 carbon atoms or straight-chain alkenyl having 8 to 24 carbon atoms and $R^2$ represents straight-chain alkyl having 8 to 24 carbon atoms or straight-chain alkenyl having 8 to 24 carbon atoms;

Y represents hydroxyl, straight-chain or branched alkoxy having 1 to 6 carbon atoms, or carboxyl which may be protected;

n is an integer of 10 to 230; and wherein the fine particles are formed by emulsifying said compound.

6. The emulsified composition according to claim 5, wherein the fine particles further comprise a drug therein and the composition is suitable for transferring the drug to a specific tissue site in a mammal.

7. The emulsified composition according to claim 5, wherein the fine particles have an average particle diameter of 100 nm or less.

8. The emulsified composition according to claim 5, wherein the fine particles further comprise phospholipid and are in the form of a liposome.

9. The emulsified composition according to claim 8, wherein the liposome further comprises a drug therein and the composition is suitable for transferring the drug to a specific tissue site in a mammal.

10. The emulsified composition according to claim 9, wherein the liposome further comprises one selected from a group consisting of cholesterol, a dialkyl phosphate, a positive charge interface substance and an antioxidant.

11. The emulsified composition according to claim 5, wherein the fine particles further comprise a phospholipid and a lipid as a core and the fine particles are in the form of a lipid emulsion.

12. The emulsified composition according to claim 10, wherein the lipid emulsion further comprises a drug in the core and the composition is suitable for transferring the drug to a specific tissue site in a mammal.

13. The emulsified composition according to claim 9, wherein the lipid emulsion further comprises one selected from the group consisting of glycerin, sugar, sugar alcohol, and a surface active agent.

14. The emulsified composition according to claim 5, wherein the fine particles further comprising a lipid as a core and are in the form of a micell.

15. The emulsified composition according to claim 12, wherein the micell further comprises a drug in the core and the composition is suitable for transferring the drug to a specific tissue site in a mammal.

16. The emulsified composition according to claim 5 which is in the form of a lipid emulsion, liposome or micell.

17. A method for transferring a drug to a specific tissue site in a mammal, comprising the step of administering an emulsified composition comprising fine particles comprising the compound represented by the following formula (I)

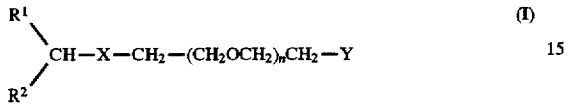

(I)

wherein $R^1$ represents straight-chain alkyl having 8 to 24 carbon atoms, straight-chain alkenyl having 8 to 24 carbon atoms, $R^3$—O—$(CH_2)$—, $R^3$—CO—O—$(CH_2)$—, $R^3$—O—CO—$(CH_2)_m$— or $R^3$—CO—NH—$(CH_2)_m$— where $R^3$ represents-straight-chain alkyl having 7 to 24 carbon atoms or straight-chain alkenyl having 7 to 24 carbon atoms, and m is an integer of 1 to 6;

$R^2$ represents straight-chain alkyl having 8 to 24 carbon atoms, straight-chain alkenyl having 8 to 24 carbon atoms, $R^3$—O—, $R^3$—CO—O— or $R^3$—O—CO— where $R^3$ is as defined above;

X represents —CO—NH—, —CO—O—, —NH—CO—$CH_2$—O— or —$CH_2$—O—CO—$CH_2$—O—, provided that when X represents —CO—O—, $R^1$ and $R^2$ do not represent $R^3$—O—CO—$(CH_2)_m$— or $R^3$—O—CO—; when X represents —NH—CO—$CH_2$—O—, $R^1$ and $R^2$ independently represent $R^3$—O—CO—$(CH_2)_m$— or $R^3$—O—CO—; when X represents —$CH_2$—O—CO—$CH_2$—O—, $R^1$ represents straight-chain alkyl having 8 to 24 carbon atoms or straight-chain alkenyl having 8 to 24 carbon atoms and $R^2$ represents straight-chain alkyl having 8 to 24 carbon atoms or straight-chain alkenyl having 8 to 24 carbon atoms;

Y represents hydroxyl, straight-chain or branched alkoxy having 1 to 6 carbon atoms, or carboxyl which may be protected;

n is an integer of 10 to 230; and wherein the fine particles are formed by emulsifying said compound, to the mammal.

* * * * *